United States Patent [19]
Marfat

[11] Patent Number: 5,958,953
[45] Date of Patent: Sep. 28, 1999

[54] SUBSTITUTED INDAZOLE DERIVATIVES

[75] Inventor: Anthony Marfat, Stonington, Conn.

[73] Assignee: Pfizer Inc, New York, N.Y.

[21] Appl. No.: 08/882,275

[22] Filed: Jun. 25, 1997

Related U.S. Application Data

[60] Provisional application No. 60/021,072, Jun. 27, 1996, abandoned.

[51] Int. Cl.[6] .......................... A61K 31/44; C07D 401/04
[52] U.S. Cl. .......................... 514/333; 514/338; 546/256; 546/275.7
[58] Field of Search .............................. 546/275.7, 256; 514/333, 338

[56] References Cited

U.S. PATENT DOCUMENTS 5,776,932   7/1998   Schindler et al. ...................... 514/274

OTHER PUBLICATIONS

CA 74:141628, Land et al., 1971.

Primary Examiner—Jane Fan
Attorney, Agent, or Firm—Peter C. Richardson; Paul H. Ginsburg; Raymond M. Speer

[57] ABSTRACT

The invention relates to compounds of the formula

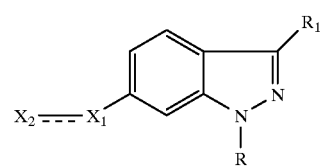

and to pharmaceutically acceptable salts thereof, wherein the broken line in formula I indicates a single or double bond, and wherein R, $R_1$, $X_1$ and $X_2$ are as defined herein. The invention further relates to pharmaceutical compositions containing the compounds of formula I, and to methods of inhibiting phosphodiesterase type IV or the production of tumor necrosis factor in a mammal by administering the compounds of formula I to said mammal.

17 Claims, No Drawings

SUBSTITUTED INDAZOLE DERIVATIVES

REFERENCE TO COPENDING APPLICATIONS

Reference is made to the following copending applications which refer to subject matter potentially related to that of the present application:

Application Ser. No. 08/963,904 filed Apr. 1, 1997 (Attorney Docket No. PC9281B); which is a continuation-in-part of PCT application PCT/IB 97/00323 designating the United States, filed in the U.S. Receiving Office on Apr. 1, 1997, and published as WO 97/42174 on Nov. 13, 1997; which claims priority from U.S. Provisional Application Ser. No. 60/016861 filed May 3, 1996, now abandoned;

application Ser. No. PCT/IB 97/01023 designating the United States, filed in the U.S. Receiving Office on Aug. 25, 1997 (Attorney Docket No. PC9282A) and published as WO 98/09961 on March 12, 1998; which claims priority from U.S. Provisional Application Ser. No. 60/025446 filed Sep. 4, 1996, now abandoned;

Application Ser. No. 08/869,358 filed Jun. 5, 1997 (Attorney Docket No. PC9283A); which is a continuation of PCT Application PCT/IB 97/00630 designating the United States, filed in the U.S. Receiving Office on Jun. 2, 1997, and published as WO 97/49702 on Dec. 31, 1997; which claims priority from U.S. Provisional Application Ser. No. 60/020385 filed Jun. 25, 1996, now abandoned; and Application Ser. No. 08/882,275 filed Jun. 25, 1997 (the present application, Attorney Docket No. PC9284A); which claims priority from U.S. Provisional Application Ser. No. 60/021072 filed Jun. 27, 1996, now abandoned.

This patent application is a non-provisional U.S. application that is based on U.S. provisional patent application No. 60/021,072, filed Jun. 27, 1996, from which priority is claimed under 35 U.S.C. §119(e).

This invention relates to novel indazole analogs that are selective inhibitors of phosphodiesterase (PDE) type IV and the production of tumor necrosis factor (TNF), and as such are useful in the treatment of asthma, arthritis, bronchitis, chronic obstructive airway disease, psoriasis, allergic rhinitis, dermatitis, and other inflammatory diseases, central nervous system disorders such as depression and multi-infarct dementia, AIDS, septic shock and other diseases involving the production of TNF. This invention also relates to a method of using such compounds in the treatment of the foregoing diseases in mammals, especially humans, and to pharmaceutical compositions containing such compounds.

Since the recognition that cyclic adenosine phosphate (AMP) is an intracellular second messenger (E. W. Sutherland, and T. W. Rall, *Pharmacol. Rev.*, 12, 265, (1960)), inhibition of the phosphodiesterases has been a target for modulation and, accordingly, therapeutic intervention in a range of disease processes. More recently, distinct classes of PDE have been recognized (J. A. Beavo et al., *Trends in Pharm. Sci.* (*TIPS*), 11, 150, (1990)), and their selective inhibition has led to improved drug therapy (C. D. Nicholson, M. S. Hahid, *TIPS*, 12, 19, (1991)). More particularly, it has been recognized that inhibition of PDE type IV can lead to inhibition of inflammatory mediator release (M. W. Verghese et al., *J. Mol. Cell Cardiol.*, 12 (Suppl. II), S 61, (1989)) and airway smooth muscle relaxation (T. J. Torphy in "Directions for New Anti-Asthma Drugs," eds S. R. O'Donnell and C. G. A. Persson, 1988, 37 Birkhauser-Verlag). Thus, compounds that inhibit PDE type IV, but which have poor activity against other PDE types, would inhibit the release of inflammatory mediators and relax airway smooth muscle without causing cardiovascular effects or antiplatelet effects. It has also been disclosed that PDE IV inhibitors are useful in the treatment of diabetes insipidus (Kidney Int. 37:362, 1990; Kidney Int. 35:494) and central nervous system disorders such as depression and multi-infarct dementia (PCT international application WO 87/06576 (published Nov. 5, 1987)).

TNF is recognized to be involved in many infectious and auto-immune diseases (W. Friers, *Fed. of Euro. Bio. Soc.* (*FEBS*) Letters, 285, 199, (1991)).

SUMMARY OF THE INVENTION

The present invention relates to compounds of the formula I

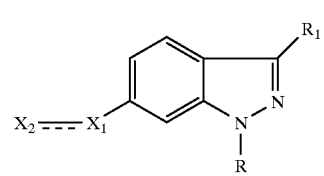

and to pharmaceutically acceptable salts thereof, wherein:

the broken line indicates a single or double bond;

$X_1$ is —$CR_2R_3$ where said broken line indicates a single bond or —$CR_3$ where said broken line indicates a double bond;

$X_2$ is —$CR_5R_7R_8$ or —$C(=NOR_{11})R_{12}$ where said broken line indicates a single bond or —$CR_7R_8$ where said broken line indicates a double bond;

R is H, $C_1$–$C_6$ alkyl, —$(CH_2)_m(C_3$–$C_7$ cycloalkyl), —$(CH_2)_m(C_3$–$C_9$ heterocyclyl), wherein m is 0 to 2, ($C_1$–$C_6$ alkoxy)$C_1$–$C_6$ alkyl, $C_2$–$C_6$ alkenyl, or —$(Z_1)_b(Z_2)_c(C_6$–$C_{10}$ aryl) wherein b and c are independently 0 or 1, $Z_1$ is $C_1$–$C_6$ alkylene or $C_2$–$C_6$ alkenylene, and $Z_2$ is O, S, $SO_2$, or $NR_5$, and wherein said R groups are optionally substituted by one or more substituents independently selected from the group consisting of halo, hydroxy, $C_1$–$C_5$ alkyl, $C_2$–$C_5$ alkenyl, $C_1$–$C_5$ alkoxy, $C_3$–$C_6$ cycloalkoxy, trifluoromethyl, nitro, —$CO_2R_5$, —$C(O)NR_5R_6$, —$NR_5R_6$ and —$SO_2NR_5R_6$;

$R_1$ is H, $C_1$–$C_7$ alkyl, $C_2$–$C_3$ alkenyl, phenyl, $C_3$–$C_7$ cycloalkyl, or ($C_3$–$C_7$ cycloalkyl)$C_1$–$C_2$ alkyl, wherein said alkyl, alkenyl and phenyl $R_1$ groups are optionally substituted by 1 to 3 substituents independently selected from the group consisting of methyl, ethyl, trifluoromethyl, and halo;

$R_2$ is H, hydroxy, halo or —$OR_9$;

each $R_3$ is independently selected from the group consisting of cyano, cyanomethyl, benzyloxy, $R_5$, —$CO_2R_5$, —$CO_2(CH_2)_n(C_6$–$C_{10}$ aryl), —$C(Y)NR_5R_6$, —$C(Y)NR_5(CH_2)_n(C_6$–$C_{10}$ aryl), —$(CH_2)_i(C_6$–$C_{10}$ aryl) and —$(CH_2)_n(5$–$10$ membered heteroaryl), wherein n is 0 to 3, each $R_3$ group is optionally substituted by 1 to 3 $R_4$ groups, and each $R_3$ group is optionally substituted by one $R_{10}$ group;

each $R_4$ is independently selected from the group consisting of halo, cyano, nitro, $C_1$–$C_6$ alkyl, $C_2$–$C_6$ alkenyl, —$OR_5$, $C_3$–$C_7$ cycloalkoxy, —$NR_5R_6$, —$NR_5OR_6$, —$S(O)_mR_5$ wherein m is 0 to 2, —$CO_2R_5$, —$C(O)R_5$, —$SO_2NR_5R_6$, —$C(O)NR_5R_6$, —CR$_5$R$_6$SO$_2$NR$_5$R$_6$, —CR$_5$R$_6$C(O)NR$_5$R$_6$, —NHSO$_2$R$_5$, —NHSO$_2$NR$_5$R$_6$, —NHC(O)NR$_5$R$_6$, —NHC(O)(C$_1$–C$_6$ alkyl) and —NHC(O)O(C$_1$–C$_6$ alkyl);

each R$_5$ and R$_6$ is independently H or C$_1$–C$_6$ alkyl;

R$_7$ is R$_3$, 2-oxo-pyridyl, 3-oxo-pyridyl, 4-oxo-pyridyl, 2-oxo-pyrrolyl, 4-oxo-thiazolyl, 4-oxo-piperidyl, 2-oxo-quinolyl, 4-oxo-quinolyl, 1-oxo-isoquinolyl, 4-oxo-oxazolyl, 5-oxo-pyrazolyl, 5-oxo-isoxazolyl, or 4-oxo-isoxazolyl, wherein each of said R$_7$ groups is optionally substituted by 1 to 3 R$_4$ groups;

R$_8$ is R$_5$, cyano, —(CH$_2$)$_p$(C$_6$–C$_{10}$ aryl) or —(CH$_2$)$_p$(5–10 membered heteroaryl), wherein p is 1 to 3 and wherein said R$_8$ substituents are optionally substituted by 1 to 3 R$_4$ substituents;

R$_9$ is formyl, carbamoyl, thiocarbamyl, C$_1$–C$_6$ alkyl, C$_2$–C$_6$ alkenyl, (C$_1$–C$_4$ alkoxy)C$_1$–C$_4$ alkyl, or C$_1$–C$_6$ alkanoyl, wherein the alkyl moieties of said R$_9$ groups are optionally substituted by 1 to 3 substituents independently selected from halo, hydroxy, and C$_1$–C$_4$ alkoxy;

R$_{10}$ is cyclobutyl, cyclopentyl, cyclohexyl, 2-cyclobuten-1-yl, 2-cyclopenten-1-yl, 3-cyclopenten-1-yl, 2,4-cyclopentadien-1-yl, 3,5-cyclohexadien-1-yl, pyrrolyl, pyrrolidinyl, dioxolanyl, imidazolyl, oxazolyl, imidazolidinyl, pyrazolyl, pyrazolidinyl, pyranyl, piperidinyl, 1,4-dioxanyl, morpholinyl, 1,4-dithianyl, thiomorpholinyl, piperazinyl, 1,3,5-trithianyl, oxazinyl, isoxazinyl, oxathiazinyl, or oxadiazinyl, wherein said R$_{10}$ substituents are optionally substituted by 1 or 2 C$_1$–C$_2$ alkyl;

R$_{11}$ is H, C$_1$–C$_6$ alkyl, C$_2$–C$_6$ alkenyl, C$_2$–C$_6$ alkynyl, —C(Y)NR$_5$R$_6$, —C(Y)NH(C$_6$–C$_{10}$ aryl), —C(Y)(C$_1$–C$_6$ alkoxy), —C(Y)(C$_6$–C$_{10}$ aryloxy), or —C(Y)(C$_1$–C$_6$ alkyl);

R$_{12}$ is phenyl or pyridinyl, wherein said R$_{12}$ substituents are optionally substituted by 1 to 3 substituents independently selected from halo, C$_1$–C$_4$ alkyl, hydroxy, C$_1$–C$_4$ alkoxy, —NR$_5$R$_6$ and —S(O)$_m$R$_5$ wherein m is 0 to 2; and, Y is O or S.

Preferred compounds of formula I include those wherein R$_1$ is ethyl and R is cyclopentyl, cyclohexyl, or C$_6$–C$_{10}$ aryl.

Other preferred compounds of formula I include those wherein R$_3$ is —(CH$_2$)$_n$(C$_6$–C$_{10}$ aryl) or —(CH$_2$)$_n$(5–10 membered heteroaryl), wherein n is 0 to 3, and, more preferably, wherein R$_3$ is phenyl or pyridin-4-yl.

Other preferred compounds of formula I include those wherein R$_7$ is —(CH$_2$)$_n$(5–10 membered heteroaryl), wherein n is 0 to 3, and, more preferably, wherein R$_7$ is pyridin-4-yl.

Specific embodiments of the compounds of formula I include those wherein the broken line indicates a single bond, R$_2$ is H, R$_3$ is phenyl, 3-methyl-phenyl, 4-pyridyl, 2-furyl, 2-thienyl, or 2-methoxy-phenyl, R$_5$ is H, R$_8$ is H, and R$_7$ is 4-pyridyl, 3-methyl-4-imidazolyl, 3,5-dichloro-4-pyridyl, or 4-pyrimidinyl.

Other specific embodiments of the compounds of formula I include those wherein the broken line indicates a double bond, R$_3$ is phenyl, 4-methoxy-phenyl, 2-furyl, 2-thienyl, 4-fluoro-phenyl, 4-trifluoromethyl-phenyl or 2-methoxy-phenyl, R$_8$ is H, and R$_7$ is 4-pyridyl.

Other specific embodiments of the compounds of formula I include those wherein the broken line indicates a single bond, R$_2$ is H, R$_5$ is H, R, is H, R$_8$ is cyano, and R$_7$ is 4-pyridyl optionally substituted by 1 or 2 chloro or —NR$_5$R$_6$.

Other specific embodiments of the compounds of formula I include those wherein the broken line indicates a double bond, R$_3$ is H, R$_8$ is H, and R$_7$ is 4-pyridyl or phenyl optionally substituted by 1 or 2 chloro groups.

Other specific embodiments of the compounds of formula I include those wherein the broken line indicates a single bond, R$_2$ is H, R$_3$ is 4-[4-(4,4-dimethyl-2-oxazolinyl) phenyl, R$_5$ is H, R$_8$ is H, and R$_7$ is 4-pyridyl.

Other specific embodiments of the compounds of formula I include those wherein the broken line indicates a single bond, R$_2$ is H, R$_3$ is phenyl, R$_5$ is H, R$_8$ is H, and R$_7$ is 4,5-dihydro-5-oxo-3-isoxazolinyl, 4,5-dihydro-5-oxo-pyrazinyl, or 2-oxo-4-pyridinyl.

Other specific embodiments of the compounds of formula I include those wherein the broken line indicates a single bond, R$_2$ is H, R$_3$ is benzyloxy, R$_5$ is H, R$_8$ is H, and R$_7$ is 4-pyridinyl.

Other specific embodiments of the compounds of formula I include those wherein the broken line indicates a single bond, R$_2$ is H, R$_3$ is H, and X$_2$ is —C(=NOR$_{11}$)R$_{12}$.

Specific preferred compounds include the following:

1-(1-cyclopentyl-3-ethyl-1H-indazol-6-yl)-1,2-di-pyridin-4-yl-ethanol;

1-cyclopentyl-6-(1,2-di-pyridin-4-yl-vinyl)-3-ethyl-1H-indazole;

1-cyclopentyl-6-(1,2-di-pyridin-4-yl-ethyl)-3-ethyl-1H-indazole;

1-(1-cyclopentyl-3-ethyl-1H-indazol-6-yl)-1-phenyl-2-pyridin-4-yl-ethanol;

1-cyclopentyl-3-ethyl-6-(1-phenyl-2-pyridin-4-yl-vinyl)-1H-indazole;

1-cyclopentyl-3-ethyl-6-(1-phenyl-2-pyridin-4-yl-ethyl)-1H-indazole;

and pharmaceutically acceptable salts of the foregoing compounds.

Other specific preferred compounds include the following:

1-(1-cyclohexyl-3-ethyl-1H-indazol-6-yl)-1,2-di-pyridin-4-yl-ethanol;

1-cyclohexyl-6-(1,2-di-pyridin-4-yl-vinyl)-3-ethyl-1H-indazole;

1-cyclohexyl-6-(1,2-di-pyridin-4-yl-ethyl)-3-ethyl-1H-indazole;

1-(1-cyclohexyl-3-ethyl-1H-indazol-6-yl)-1-phenyl-2-pyridin-4-yl-ethanol;

1-cyclohexyl-3-ethyl-6-(1-phenyl-2-pyridin-4-yl-vinyl)-1H-indazole;

1-cyclohexyl-3-ethyl-6-(1-phenyl-2-pyridin-4-yl-ethyl)-1H-indazole;

and pharmaceutically acceptable salts of the foregoing compounds.

The present invention further relates to a pharmaceutical composition for the inhibition of phosphodiesterase (PDE) type IV or the production of tumor necrosis factor (TNF) comprising a therapeutically effective amount of a compound according to formula I, as defined above, or a pharmaceutically acceptable salt thereof, and a pharmaceutically acceptable carrier.

The present invention further relates to a method for the inhibition of phosphodiesterase (PDE) type IV or the production of tumor necrosis factor (TNF) in a mammal, such as a human, by administering to said mammal a therapeutically effective amount of a compound according to formula I, as defined above, or a pharmaceutically acceptable salt thereof.

The present invention further relates to a pharmaceutical composition for the prevention or treatment of asthma, joint inflammation, rheumatoid arthritis, gouty arthritis, rheumatoid spondylitis, osteoarthritis, and other arthritic conditions; sepsis, septic shock, endotoxic shock, gram negative sepsis, toxic shock syndrome, acute respiratory distress syndrome, cerebal malaria, chronic pulmonary inflammatory disease, silicosis, pulmonary sarcoidosis, bone resorption diseases, reperfusion injury, graft vs. host reaction, allograft rejections, fever and myalgias due to infection, such as influenza, cachexia secondary to infection or malignancy, cachexia secondary to human acquired immune deficiency syndrome (AIDS), AIDS, HIV, ARC (AIDS related complex), keloid formation, scar tissue formation, Crohn's disease, ulcerative colitis, pyresis, multiple sclerosis, type 1 diabetes mellitus, diabetes insipidus, autoimmune diabetes, systemic lupus erythematosis, bronchitis, chronic obstructive airway disease, psoriasis, Bechet's disease, anaphylactoid purpura nephritis, chronic glomerulonephritis, inflammatory bowel disease, leukemia, allergic rhinitis, dermatitis, depression or multi-infarct dementia, comprising a therapeutically effective amount of a compound according to formula I, as defined above, or a pharmaceutically acceptable salt, thereof together with a pharmaceutically acceptable carrier.

This invention further relates to a method of treating or preventing the foregoing specific diseases and conditions in a mammal, such as a human, by administering to said mammal a therapeutically effective amount of a compound according to formula I, as defined above, or a pharmaceutically acceptable salt thereof.

The term "halo", as used herein, unless otherwise indicated, means fluoro, chloro, bromo or iodo. Preferred halo groups are fluoro, chloro and bromo.

The term "alkyl", as used herein, unless otherwise indicated, includes saturated monovalent hydrocarbon radicals having straight, cyclic or branched moieties.

The term "alkoxy", as used herein, unless otherwise indicated, includes —O-alkyl groups wherein alkyl is as defined above.

The term "alkanoyl", as used herein, unless otherwise indicated, includes —C(O)-alkyl groups wherein alkyl is as defined above.

The term "cycloalkyl", as used herein, unless otherwise indicated, includes saturated monovalent cyclo hydrocarbon radicals including cyclobutyl, cyclopentyl and cycloheptyl.

The term "aryl", as used herein, unless otherwise indicated, includes an organic radical derived from an aromatic hydrocarbon by removal of one hydrogen, such as phenyl or naphthyl.

The term "heterocyclyl", as used herein, unless otherwise indicated, includes aromatic and non-aromatic heterocyclic groups containing one or more heteroatoms each selected from O, S and N. The heterocyclic groups include benzofused ring systems and ring systems substituted with an oxo moiety. An example of a 5-membered heterocyclic group is thiazolyl, and an example of a 10-membered heterocyclic group is quinolinyl. Examples of non-aromatic heterocyclic groups are pyrrolidinyl, piperidino, morpholino, thiomorpholino and piperazinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl and thiazolyl. Heterocyclic groups having a fused benzene ring include benzimidazolyl.

The term "heteroaryl", as used herein, unless otherwise indicated, includes aromatic heterocyclic groups wherein heterocyclic is as defined above.

The phrase "pharmaceutically acceptable salt(s)", as used herein, unless otherwise indicated, includes salts of acidic or basic groups which may be present in the compounds of formula I.

Certain compounds of formula I may have asymmetric centers and therefore exist in different enantiomeric forms, and certain compounds of formula I may exist as cis and trans isomers. This invention relates to the use of all optical isomers and stereoisomers of the compounds of formula I and mixtures thereof. The compounds of formula I may also exist as tautomers. This invention relates to the use of all such tautomers and mixtures thereof.

DETAILED DESCRIPTION OF THE INVENTION

The following reaction schemes 1–3 illustrate the preparation of the compounds of the present invention. Unless otherwise indicated, R, $R_1$, $R_3$, $R_5$, $R_7$ and $R_8$ in the reaction schemes are as defined above.

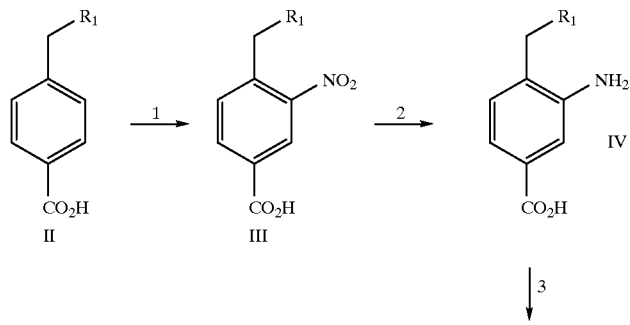

-continued
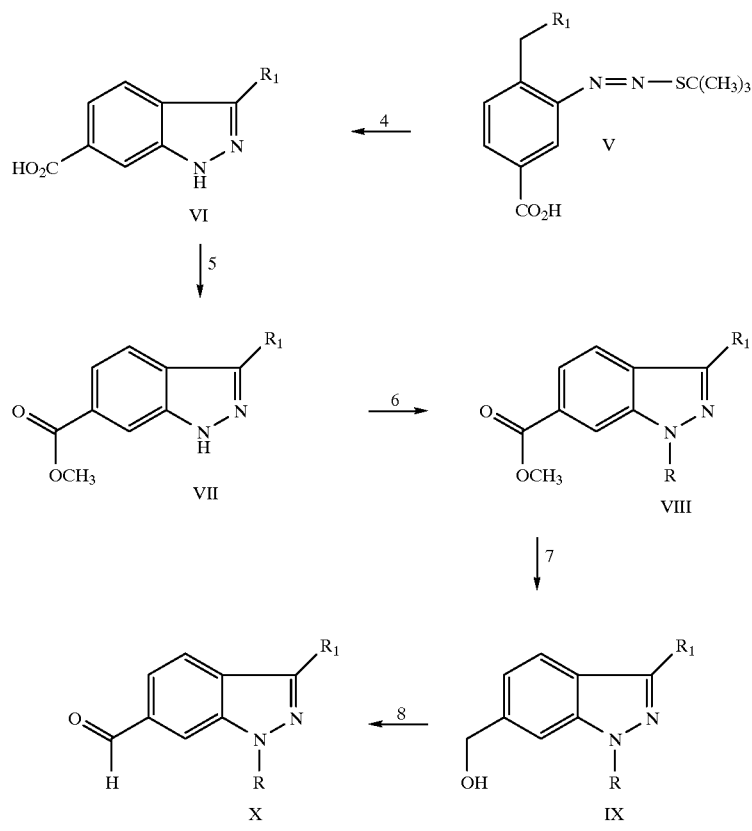
Scheme 2
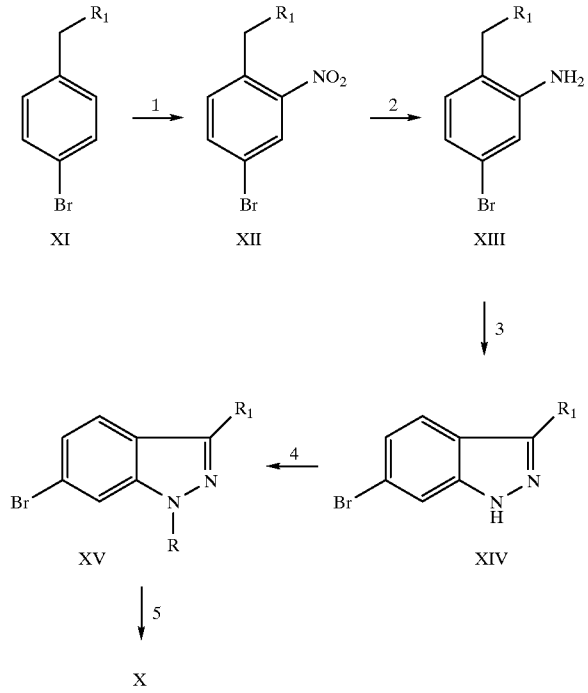

-continued

Scheme 3

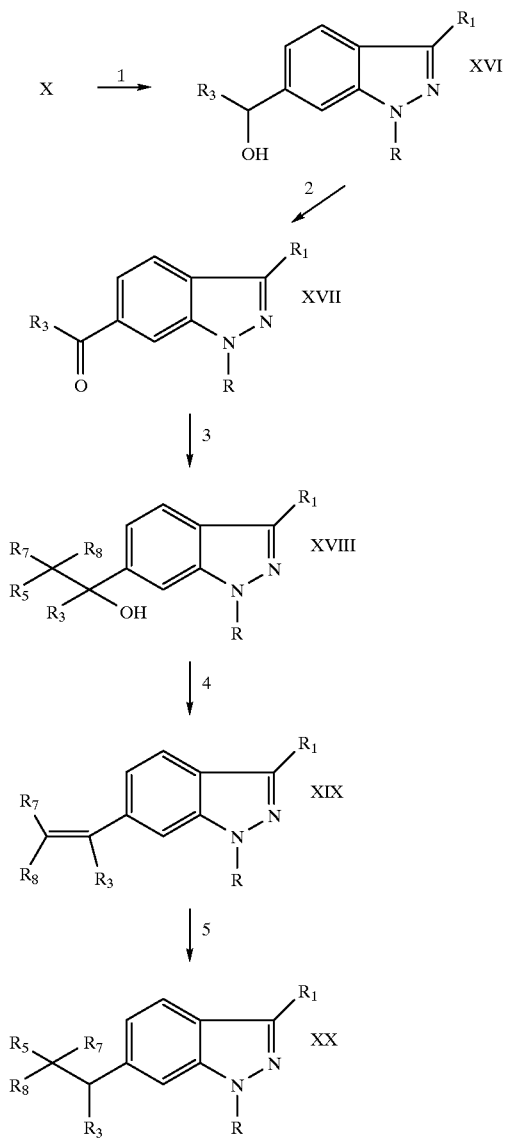

The preparation of compounds of formula I can be carried out by one skilled in the art according to one or more of the synthetic methods outlined in Schemes 1–3 above and the examples referred to below. In step 1 of Scheme 1, the carboxylic acid of formula II, which is available from known commercial sources or can be prepared according to methods known to those skilled in the art, is nitrated under standard conditions of nitration ($HNO_3/H_2SO_4$, 0° C.) and the resulting nitro derivative of formula III is hydrogenated in step 2 of Scheme 1 using standard hydrogenation methods ($H_2$—Pd/C under pressure) at ambient temperature (20–25° C.) for several hours (2–10 hours) to provide the compound of formula IV. In step 3 of scheme 1, the amino benzoic acid of formula IV is reacted with a base such as sodium carbonate under aqueous conditions and gently heated until mostly dissolved. The reaction mixture is chilled to a lower temperature (about 0° C.) and treated with sodium nitrate in water. After about 15 minutes, the reaction mixture is slowly transferred to an appropriate container holding crushed ice and a strong acid such as hydrochloric acid. The reaction mixture is stirred for 10–20 minutes and then added, at ambient temperature, to a solution of excess t-butyl thiol in an aprotic solvent such as ethanol. The reaction mixture is acidified to a pH of 4–5 through addition of an inorganic base, preferably saturated aqueous $Na_2CO_3$, and the reaction mixture is allowed to stir at ambient temperature for 1–3 hours. Addition of brine to the reaction mixture, followed by filtration, provides the sulfide of formula V.

In step 4 of Scheme 1, the sulfide of formula V is converted to the corresponding indazole carboxylic acid of formula VI by reacting the sulfide of formula V with a strong base, preferably potassium t-butoxide, in dimethyl sulfoxide (DMSO) at ambient temperature. After stirring for several hours (1–4 hours), the reaction mixture is acidified with a strong acid, such as hydrochloric or sulfuric acid, and then extracted using conventional methods. In step 5 of Scheme 1, the indazole carboxylic acid of formula VI is converted to the corresponding ester of formula VII by conventional methods known to those skilled in the art. In step 6 of Scheme 1, the compound of formula VIII is provided through alkylation of the ester of formula VII by subjecting the ester to conventional alkylation conditions (strong base/ various alkylating agents and, optionally, a copper catalyst such as $CuBr_2$) in a polar aprotic solvent, such as tetrahydrofuran (THF), N-methylpyrrolidinone or dimethylformamide (DMF), at ambient or higher temperature (25–200° C.) for about 6–24 hrs, preferably about 12 hours. In step 7 of Scheme 1, the compound of formula VIII is converted to the corresponding alcohol of formula IX by following conventional methods known to those skilled in the art for reducing esters to alcohols. Preferably, the reduction is effected through use of a metal hydride reducing agent, such as lithium aluminum hydride, in a polar aproptic solvent at a low temperature (about 0° C.). In step 8 of Scheme 1, the alcohol of formula IX is oxidized to the corresponding aldehyde of formula X according to conventional methods known to those skilled in the art. For example, the oxidation can be effected through use of a catalytic amount of tetrapropylammonium perrutenate and excess N-methylmorpholine-N-oxide, as described in J. Chem. Soc., Chem. Commun., 1625 (1987), in an anhydrous solvent, preferably methylene chloride.

Scheme 2 provides an alternative method of preparing the aldehyde of formula X. In step 1 of Scheme 2, the compound of formula XI is nitrated using conventional nitration conditions (nitric and sulfuric acid) to provide the compound of formula XII. In step 2 of Scheme 2, the nitro derivative of formula XII is reduced to the corresponding amine of formula XIII according to conventional methods known to those skilled in the art. Preferably, the compound of formula XII is reduced to the amine of formula XIII using anhydrous stannous chloride in an anhydrous aprotic solvent such as ethanol. In step 3 of Scheme 2, the amine of formula XII is converted to the corresponding indazole of formula XIV by preparing the corresponding diazonium tetrafluoroborates as described in A. Roe, *Organic Reactions,* Vol. 5, Wiley, N.Y., 1949, pp. 198–206, followed by phase transfer catalyzed cyclization as described in R. A. Bartsch and I. W. Yang, J. Het. Chem. 21, 1063 (1984). In step 4 of Scheme 2, alkylation of the compound of formula XIV is performed using standard methods known to those skilled in the art (i.e. strong base, polar aprotic solvent and an alkyl halide) to provide the N-alkylated compound of formula XV. In step 5 of Scheme 2, the compound of formula XV is subjected to metal halogen exchange employing an alkyl lithium, such as n-butyl lithium, in a polar aprotic solvent, such as THF, at low temperature (−50° C. to 100° C. (−78° C. preferred)) followed by quenching with DMF at low temperature and warming to ambient temperature to provide the aldehyde intermediate of formula X.

Scheme 3 illustrates the preparation of the compounds of formula I. In step 1 of Scheme 3, the intermediate aldehyde of formula X is reacted with a compound of formula $R_3$—Li, wherein $R_3$ is as defined above, in THF at a temperature within the range of about −78° C. to ambient temperature (20–25° C.) for a period of about 30 minutes to 3 hours to provide the alcohol intermediate of formula XVI. In step 2 of Scheme 3, the intermediate of formula XVI is reacted in the presence of tetrapropylammonium perruthenate (VII) and 4A molecular sieves in N-methylmorpholine N-oxide and methylene chloride at ambient temperature for about 1 hour to provide the ketone intermediate of formula XVII. In an alternative, the ketone intermediate of formula XVII can be synthesized by reacting the intermediate of formula XV with a compound of formula $R_3$—CN, wherein $R_3$ is as defined above, in the presence of n-butyllithium in THF at a temperature of about −78° C. for about 45 minutes and then warming the mixture to −10° C. for about 30 minutes to provide the intermediate of formula XVII. In step 3 of Scheme 3, the intermediate of formula XVII is reacted with a compound of formula $CHR_5R_7R_8$, wherein $R_5$, $R_7$, and $R_8$ are as defined above, in the presence of n-butyllithium in THF at a temperature of about −78° C. for about 1 hour and then warming the mixture to ambient temperature for about 30 minutes to provide the intermediate of formula XVIII. In step 4 of Scheme 3, the intermediate of formula XVIII is reacted in the presence of p-toluenesulfonic acid and toluene and heated to reflux for about 7 hours to provide the compound of formula XIX which corresponds to the compound of formula I wherein the dashed line indicates a double bond. This reaction proceeds directly where $R_5$ or $R_8$ is hydrogen. In step 5 of Scheme 3, the compound of formula XIX is hydrogenated in the presence of palladium on carbon in ethanol and triethylamine under 25 psi $H_2$ at ambient temperature for about 3.5 hours followed by separation of the reaction product and dissolution of the reaction product in ether and 1 N hydrochloric acid to provide the compound of formula XX. The compound of formula XX corresponds to the compound of formula I wherein the dashed line indicates a single bond.

The compounds of formula I can also be prepared following one or more synthetic methods that are disclosed in published patent applications. In particular, using the intermediates described in Schemes 1–3, referred to above, in particular the intermediates of formulas VIII, X, and XV, those skilled in the art can prepare the compounds of formula I using analogous synthetic methods that have been described for compounds in which a phenyl ring is substituted for the indazole ring in the compounds of formula I. Such analogous synthetic methods are disclosed in the following published PCT international applications: WO 94/14742 (published Jul. 7, 1994); WO 94/14800 (published Jul. 7, 1994); WO 94/20446 (published Sep. 15, 1994); WO 94/20455 (published Sep. 15, 1994); WO 95/17392 (published Jun. 29, 1995); WO 95/17399 (published Jun. 29, 1995), WO 95/35284, WO 95/35285, and WO 96/00215. The foregoing published PCT international patent applications are incorporated herein by reference in their entirety.

Specifically, the compounds of formula I wherein $R_3$ and $R_7$ are independently —$(CH_2)_n(C_6$–$C_{10}$ aryl) or —$(CH_2)_n$ (5–10 membered heteroaryl) and $R_8$ is H or $C_1$–$C_6$ alkyl can be prepared by following analogous synthetic methods disclosed in WO 94/14742 and WO 94/14800, both of which are referred to above. The compounds of formula I wherein $R_3$ and $R_7$ are independently H, $C_1$–$C_6$ alkyl, cyano, cyanomethyl, —$CO_2(CH_2)_n(C_6$–$C_{10}$ aryl), —$C(Y)NR_5R_6$ or —$C(Y)NR_5(CH_2)_n(C_6$–$C_{10}$ aryl) and $R_8$ is —$(CH_2)_p$ $(C_6$–$C_{10}$ aryl) or —$(CH_2)_p(C_6$–$C_{10}$ heteroaryl) can be prepared by following analogous synthetic methods disclosed in WO 94/20446 and WO 94/20455, both of which are referred to above. The compounds of formula I wherein $R_3$ is —$(CH_2)_n(C_6$–$C_{10}$ aryl) or —$(CH_2)_n$(5–10 membered heteroaryl), and $R_7$ is 2-oxo-pyridyl, 3-oxo-pyridyl, 4-oxo-pyridyl, 2-oxo-pyrrolyl, 4-oxo-thiazolyl, 4-oxo-piperidyl, 2-oxo-quinolyl, 4-oxo-quinolyl, 1-oxo-isoquinolyl, 4-oxo-oxazolyl, 5-oxo-pyrazolyl, 5-oxo-isoxazolyl, or 4-oxo-isoxazolyl, can be prepared by following analogous methods disclosed in WO 95/17392, which is referred to above. The compounds of formula I wherein $R_3$ is —$(CH_2)_n(C_6$–$C_{10}$ aryl) or —$(CH_2)_n$(5–10 membered heteroaryl) optionally substituted by an $R_{10}$ substituent, and $R_7$ is —$(CH_2)_n$ $(C_6$–$C_{10}$ aryl) or —$(CH_2)_n$(5–10 membered heteroaryl), can be prepared by following analogous methods disclosed in WO 95/17399, which is referred to above. The compounds of formula I wherein $R_3$ is benzyloxy and $R_7$ is —$(CH_2)_n$ (5–10 membered heteroaryl), can be prepared by following analogous methods disclosed in WO 95/35284, which is referred to above. The compounds of formula I wherein the dashed line indicates a single bond and $X_2$ is —C(=NOR$_{11}$) $R_{12}$ can be prepared by following analogous methods disclosed in WO 96/00215, which is referred to above.

The compounds of formula I can be resolved into separate enantiomers by using a chiral LC technique according to the following conditions: column: Chiralcel® OD (250×4.6 mm); Mobile phase: 50:50:0.1 (Hexane:2-propanol:diethylamine); Flow rate: 1 mL/minute; detection: UV (230 nm); temperature: ambient (20–25° C.); injection volume: 20 µL. The compounds of formula I can also be resolved into separate enantiomers according to other techniques familiar to those skilled in the art, including those described in J. March, *Advanced Organic Chemistry*, (4th Edition, J. Wiley & Sons), 1992, pages 118–125.

The compounds of formula I that are basic in nature are capable of forming a wide variety of different salts with various inorganic and organic acids. Although such salts must be pharmaceutically acceptable for administration to humans or animals, it is often desirable in practice to initially isolate the compound of formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon evaporation of the solvent, the desired solid salt is readily obtained. The desired acid addition salt can also be precipitated from a solution of the free base in an organic solvent by adding to the solution an appropriate mineral or organic acid. Pharmaceutically acceptable salts of amino groups include hydrochloride (preferred), hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate) salts. Cationic salts of the compounds of formula I are similarly prepared except through reaction of a carboxy group, such as where $R_6$ is carboxy, with an appropriate cationic salt reagent such as sodium, potassium, calcium, magnesium, ammonium, N,N'-dibenzylethylenediamine, N-methylglucamine (meglumine), ethanolamine, tromethamine, or diethanolamine.

For administration to humans in the curative or prophylactic treatment of inflammatory diseases, oral dosages of a compound of formula I or a pharmaceutically acceptable salt thereof (the active compounds) are generally in the range of 0.1 to 1000 mg daily, in single or divided doses, for an average adult patient (70 kg). The active compounds can be administered in single or divided doses. Individual tablets or capsules should generally contain from 0.1 to 100 mg of active compound, in a suitable pharmaceutically acceptable vehicle or carrier. Dosages for intravenous administration are typically within the range of 0.1 to 10 mg per single dose as required. For intranasal or inhaler administration, the dosage is generally formulated as a 0.1 to 1% (w/v) solution. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and all such dosages are within the scope of this invention.

For administration to humans for the inhibition of TNF, a variety of conventional routes may be used including orally, parenterally, topically, and rectally (suppositories). In general, the active compound will be administered orally or parenterally at dosages between about 0.1 and 25 mg/kg body weight of the subject to be treated per day, preferably from about 0.3 to 5 mg/kg in single or divided doses. However, some variation in dosage will necessarily occur depending on the condition of the subject being treated. The person responsible for administration will, in any event, determine the appropriate dose for the individual subject.

For human use, the active compounds of the present invention can be administered alone, but will generally be administered in an admixture with a pharmaceutical diluent or carrier selected with regard to the intended route of administration and standard pharmaceutical practice. For example, they may be administered orally in the form of tablets containing such excipients as starch or lactose, or in capsules either alone or in admixture with excipients, or in the form of elixirs or suspensions containing flavoring or coloring agents. They may be injected parenterally; for example, intravenously, intramuscularly or subcutaneously. For parenteral administration, they are best used in the form of a sterile aqueous solution which may contain other substance; for example, enough salts or glucose to make the solution isotonic.

Additionally, the active compounds may be administered topically when treating inflammatory conditions of the skin and this may be done by way of creams, jellies, gels, pastes, and ointments, in accordance with standard pharmaceutical practice.

The therapeutic compounds may also be administered to a mammal other than a human. The dosage to be administered to a mammal will depend on the animal species and the disease or disorder being treated. The therapeutic compounds may be administered to animals in the form of a capsule, bolus, tablet or liquid drench. The therapeutic compounds may also be administered to animals by injection or as an implant. Such formulations are prepared in a conventional manner in accordance with standard veterinary practice. As an alternative the therapeutic compounds may be administered with the animal feedstuff and for this purpose a concentrated feed additive or premix may be prepared for mixing with the normal animal feed.

The ability of the compounds of formula I or the pharmaceutically acceptable salts thereof to inhibit PDE IV may be determined by the following assay.

Thirty to forty grams of human lung tissue is placed in 50 ml of pH 7.4 Tris/phenylmethylsulfonyl fluoride (PMSF)/sucrose buffer and homogenized using a Tekmar Tissumizer® (Tekmar Co., 7143 Kemper Road, Cincinnati, Ohio 45249) at full speed for 30 seconds. The homogenate is centrifuged at 48,000×g for 70 minutes at 4° C. The supernatant is filtered twice through a 0.22 µm filter and applied to a Mono-Q FPLC column (Pharmacia LKB Biotechnology, 800 Centennial Avenue, Piscataway, N.J. 08854) pre-equilibrated with pH 7.4 Tris/PMSF Buffer. A flow rate of 1 ml/minute is used to apply the sample to the column, followed by a 2 ml/minute flow rate for subsequent washing and elution. Sample is eluted using an increasing, step-wise NaCl gradient in the pH 7.4 Tris/PMSF buffer.

Eight ml fractions are collected. Fractions are assayed for specific $PDE_{IV}$ activity determined by [$^3$H]cAMP hydrolysis and the ability of a known $PDE_{IV}$ inhibitor (e.g. rolipram) to inhibit that hydrolysis. Appropriate fractions are pooled, diluted with ethylene glycol (2 ml ethylene glycol/5 ml of enzyme prep) and stored at −20° C. until use.

Compounds are dissolved in dimethylsulfoxide (DMSO) at a concentration of 10 mM and diluted 1:25 in water (400 μM compound, 4% DMSO). Further serial dilutions are made in 4% DMSO to achieve desired concentrations. The final DMSO concentration in the assay tube is 1%. In duplicate the following are added, in order, to a 12×75 mm glass tube (all concentrations are given as the final concentrations in the assay tube).

i) 25 μl compound or DMSO (1%, for control and blank)
ii) 25 μl pH 7.5 Tris buffer
iii) [$^3$H]cAMP (1 μM)
iv) 25 μl PDE IV enzyme (for blank, enzyme is preincubated in boiling water for 5 minutes)

The reaction tubes are shaken and placed in a water bath (37° C.) for 20 minutes, at which time the reaction is stopped by placing the tubes in a boiling water bath for 4 minutes. Washing buffer (0.5 ml, 0.1M 4-(2-hydroxyethyl)-1-piperazine-ethanesulfonic acid (HEPES)/0.1 M naci, pH 8.5) is added to each tube on an ice bath. The contents of each tube are filed to an AFF-Gel 601 column (Biorad Laboratories, P.O. Box 1229, 85A Marcus Drive, Melvile, N.Y. 11747) (boronate affinity gel, 1 ml bed volume) previously equilibrated with washing buffer. [$^3$H]cAMP is washed with 2×6 ml washing buffer, and [3H]5'AMP is then eluted with 4 ml of 0.25M acetic acid. After vortexing, 1 ml of the elution is added to 3 ml scintillation fluid in a suitable vial, vortexed and counted for [$^3$H].

$$\% \text{ inhibition} = 1 - \frac{\text{average cpm (test compound} - \text{average cmp (blank)}}{\text{average cpm (control)} - \text{average cpm (blank)}}$$

$IC_{50}$ is defined as that concentration of compound which inhibits 50% of specific hydrolysis of [$^3$H]cAMP to [$^3$H]5'AMP.

The ability of the compounds I or the pharmaceutically acceptable salts thereof to inhibit the production TNF and, consequently, demonstrate their effectiveness for treating disease involving the production of TNF is shown by the following in vitro assay:

Peripheral blood (100 mls) from human volunteers is collected in ethylenediaminetetraacetic acid (EDTA). Mononuclear cells are isolated by FICOLL/Hypaque and washed three times in incomplete HBSS. Cells are resuspended in a final concentration of 1×10$^6$ cells per ml in pre-warmed RPMI (containing 5% FCS, glutamine, pen/step and nystatin). Monocytes are plated as 1×10$^6$ cells in 1.0 ml in 24-well plates. The cells are incubated at 37° C. (5% carbon dioxide) and allowed to adhere to the plates for 2 hours, after which time non-adherent cells are removed by gentle washing. Test compounds (10 μl) are then added to the cells at 3–4 concentrations each and incubated for 1 hour. LPS (10 μl) is added to appropriate wells. Plates are incubated overnight (18 hrs) at 37° C. At the end of the incubation period TNF was analyzed by a sandwich ELISA (R&D Quantikine Kit). $IC_{50}$ determinations are made for each compound based on linear regression analysis. The following Examples and Preparations illustrate the preparation of the compounds of the present invention.

PREPARATION 1

1-Cyclopentyl-3-ethyl-1H-indazole-6-carboxylic acid methyl ester

A. 3-Nitro-4-propyl-benzoic acid. 9.44 g (57.5 mmol, 1.0 equiv) of 4-propylbenzoic acid were partially dissolved in 50 mL concentrated $H_2SO_4$ and chilled in an ice bath. A solution of 4.7 mL (74.7 mmol, 1.3 equiv) concentrated $HNO_3$ in 10 mL concentrated $H_2SO_4$ was added dropwise over 1–2 min. After stirring 1 hour at 0° C., the reaction mixture was poured into a 1 L beaker half full with ice. After stirring 10 min., the white solid that formed was filtered, washed 1×$H_2O$, and dried to give 12.01 g (100%) of the title compound: mp 106–109° C.; IR (KBr) 3200–3400, 2966, 2875, 2667, 2554, 1706, 1618, 1537, 1299, 921 cm$^{-1}$; $^1$H NMR (300 MHz, DMSO-d$_6$) δ 0.90 (t, 3H J=7.4 Hz), 1.59 (m, 2H), 2.82 (m, 2H), 7.63 (d, 1H, J=8.0 Hz), 8.12 (dd, 1H, J=1.7, 8.0 Hz), 8.33 (d, 1H, J=1.7 Hz); $^{13}$C NMR (75.5 MHz, DMSO-d$_6$) δ 14.2, 23.7, 34.2, 125.4, 130.5, 132.9, 133.6, 141.4, 149.5, 165.9; Anal. calcd for $C_{10}H_{11}NO_4 \cdot ¼H_2O$: C, 56.20; H, 5.42; N, 6.55. Found: C, 56.12; H, 5.31; N, 6.81.

B. 3-Amino-4-propyl-benzoic acid. A mixture of 11.96 g (57.2 mmol) 3-nitro-4-propyl-benzoic acid and 1.5 g 10% Pd/C, 50% water wet, in 250 mL $CH_3OH$ was placed on a Parr hydrogenation apparatus and shaken under 25 psi $H_2$ at ambient temperature (20–25° C.). After 1 hours, the reaction mixture was filtered through Celite®, and the filtrate concentrated and dried to give 9.80 g (96%) of a pale yellow crystalline solid: mp 139.5–142.5° C.; IR (KBr) 3200–2400, 3369, 3298, 2969, 2874, 2588, 1690, 1426, 1260, 916, 864 cm$^{-1}$; $^1$H NMR (300 MHz, DMSO-d$_6$) δ 0.90 (t, 3H, J=7.2 Hz), 1.52 (m, 2H), 2.42 (m, 2H), 5.08 (br s, 2H), 6.96 (d, 1H, J=7.8 Hz), 7.05 (dd, 1H, J=1.7, 7.8 Hz), 7.20 (d, 1H, J=1.7 Hz), MS (Cl, NH$_3$) m/z 180 (M+H$^+$, base); Anal. calcd for $C_{10}H_{13}NO_2 \cdot ⅓H_2O$: C, 64.85; N, 7.89; N, 7.56. Found: C, 64.69; H, 7.49; N, 7.86.

C. 3-Carboxy-6-propyl-benzenediazo t-butyl sulfide. A mixture of 8.80 g (49.1 mmol, 1.0 equiv) 3-amino-4-propyl-benzoic acid and 2.34 g (22.1 mmol, 0.45 equiv) sodium carbonate in 55 mL $H_2O$ was heated gently with a heat gun until mostly dissolved. The reaction mixture was chilled in an ice bath, and a solution of 3.73 g (54.0 mmol, 1.0 equiv) sodium nitrite in 27 mL $H_2O$ was added dropwise. After 15 minutes, the reaction mixture was transferred to a dropping funnel and added over 10 minutes to a beaker containing 55 g of crushed ice and 10.6 mL concentrated HCl. After stirring 10 minutes, the contents of the beaker were transferred to a dropping funnel and added over 5 minutes to a room temperature solution of 5.31 mL (47.1 mmol, 0.96 equiv) t-butyl thiol in 130 mL ethanol. The pH was adjusted to 4–5 by addition of saturated aqueous $Na_2CO_3$ solution, and the reaction mixture was allowed to stir 1 hour at ambient temperature (20–25° C.). 200 mL brine were added, and the mixture was filtered. The solid was washed 1×$H_2O$ and dried overnight to give 12.25 g (89%) of a brown/rust colored powder (caution-stench): mp 102° C. (dec); IR (KBr) 3200–2400, 2962, 2872, 2550, 1678, 1484, 1428, 1298, 1171 cm$^{-1}$; $^1$H NMR (300 MHz, DMSO-d$_6$) δ 0.84 (t, 3H, J=7.3 Hz), 1.48 (m, 2H), 1.55 (s, 9H), 2.42 (m, 2H), 7.29 (d, 1H, J=1.6 Hz), 7.50 (d, 1H, J=8.0 Hz), 7.86 (dd, 1H, J=1.7, 7.9 Hz), 13.18 (br s, 1H); MS (thermospray, NH$_4$OAc) m/z 281 (M+H+, base); Anal. calcd for $C_{14}H_{20}N_2O_2S$: C, 59.96; H, 7.19; N, 9.99. Found: C, 59.71; H, 7.32; N, 10.02.

D. 3-Ethyl-1H-indazole-6-carboxylic acid. A solution of 12.0 g (42.8 mmol, 1.0 equiv) 3-carboxy-6-propyl-benzenediazo t-butyl sulfide in 150 mL DMSO was added dropwise over 15 minutes to an ambient temperature solution of 44.6 g (398 mmol, 9.3 equiv) potassium t-butoxide in 200 mL dimethylsulfoxide (DMSO). After stirring 2 hours at ambient temperature, the reaction mixture was poured into 1.5 L of 0° C. 1 N HCl, stirred 5 minutes, then extracted 2×350 mL ethyl acetate. The ethyl acetate extracts (caution-stench) were combined, washed 2×250 mL H$_2$O, and dried over MgSO$_4$. Filtration, concentration of filtrate and drying gave a tan solid, which was triturated with 1 L of 1:3 Et$_2$O/Hexanes and dried to give 7.08 g (87%) of a tan crystalline powder: mp 248–251° C.; IR (KBr) 3301, 3300–2400, 2973, 2504, 1702, 1455, 1401, 1219 cm$^{-1}$; $^1$H NMR (300 MHz, DMSO-d$_6$) δ 1.31 (t, 3H, J=7.6 Hz), 2.94 (q, 2H, J=7.6 Hz), 7.63 (dd, 1H, J=1.1, 8.4 Hz), 7.81 (d, 1H, J=8.4 Hz), 8.06 (d, 1H, J=1.1. Hz), 12.95 (br s, 1H); MS (Cl, NH$_3$) m/z 191 (M+H+, base); Anal. calcd for C$_{10}$H$_{10}$N$_2$O$_2$: C, 63.14; H, 5.30; N, 14.73. Found: C, 62.66; H. 5.42; N, 14.80.

E. 3-Ethyl-1H-indazole-6-carboxylic acid methyl ester. 8.78 g (45.8 mmol, 1.1 equiv) 1-(3-dimethylaminopropyl)-3-ethylcarbodiimide hydrochloride were added in one portion to an ambient temperature solution of 7.92 g (41.6 mmol, 1.0 equiv) 3-ethyl-1H-indazole-6-carboxylic acid, 16.9 mL (416 mmol, 10 equiv) methanol and 5.59 g (45.8 mmol, 1.1 equiv) dimethylaminopyridine (DMAP) in 250 mL CH$_2$Cl$_2$. After 18 hours at room temperature, the reaction mixture was concentrated to 150 mL, diluted with 500 mL ethyl acetate, washed 2×100 mL 1 N HCl, 1×100 mL H$_2$O, 1×100 mL brine, and dried over Na$_2$SO$_4$. Filtration, concentration of filtrate and drying gave 7.8 g of a brown solid, which was purified on a silica gel column (30% to 50% ethyl acetate/hexane gradient) to give 6.41 g (75%) of a tan solid: mp 107–108° C.; IR (KBr) 3100–2950, 1723, 1222 cm$^{-1}$; $^1$H NMR (300 MHz, CDCl$_3$) δ 8.19 (m, 1H), 7.7–7.8 (m, 2H), 3.96 (s, 3H), 3.05 (q, 2H, J=7.7 Hz), 1.43 (t, 3H, 7.7 Hz); MS (Cl, NH$_3$) m/z 205 (M+H$^+$, base); Anal. calcd for C$_{11}$H$_{12}$N$_2$O$_2$: C, 64.70; H, 5.92; N, 13.72. Found: C, 64.88; H, 6.01; N, 13.96.

F. 1-Cyclopentyl-3-ethyl-1H-indazole-6-carboxylic acid methyl ester. 1.17 g (29.4 mmol, 1.05 equiv) sodium hydride, 60% oil dispersion, were added in one portion to an ambient temperature solution of 5.7 g (27.9 mmol, 1.0 equiv) 3-ethyl-1H-indazole-6-carboxylic acid methyl ester in 125 mL anhydrous DMF. After 20 min., 3.89 mL (36.6 mmol, 1.3 equiv) cyclopentyl bromide were added dropwise, and the reaction mixture allowed to stir overnight at room temperature. The mixture was then poured into 1 L H$_2$O and extracted 3×450 mL ethyl acetate. The organic extracts were combined, washed 3×400 mL H$_2$O, 1×200 mL brine, and dried over Na$_2$SO$_4$. Filtration, concentration of filtrate and drying gave an amber oil, which was purified on a silica gel column (10% ethyl acetate/hexanes, gravity) to give 5.48 g (72%) of a clear oil: $^1$H NMR (300 MHz, CDCl$_3$) δ 8.16 (d, 1H, J=1.0 Hz), 7.7 (m, 2H), 5.00 (quintet, 1H, J=7.5 Hz), 3.97 (s, 3H), 3.01 (q, 2H, J=7.6 Hz), 2.2 (m, 4H), 2.0 (m, 2H), 1.8 (m, 2H), 1.39 (t, 3H, J=7.6 Hz); HRMS calcd for C$_{16}$H$_{20}$N$_2$O$_2$: 272.1526. Found: 272.15078.

G. (1-Cyclopentyl-3-ethyl-1H-indazol-6-yl)-methanol. 7 ml (7.0 mmol, 1.0 equiv) lithium aluminum hydride, 1.0 M solution in THF, were added to a 0° C. solution of 1.02 g (7.05 mmol, 1.0 equiv) 1-cyclopentyl-3-ethyl-1H-indazole-6-carboxylic acid methyl ester in 50 mL anhydrous THF. After 20 minutes, 1 mL methanol was added cautiously, then the reaction mixture was poured into 500 mL of 5% H$_2$SO$_4$ and extracted 3×50 mL ethyl acetate. The organic extracts were combined, washed 2×40 mL H$_2$O, 1×40 mL brine, and dried over Na$_2$SO$_4$. Filtration, concentration of filtrate, and drying gave 1.58 g of a clear oil, which was purified on a silica gel column to give 1.53 g (89%) clear oil: IR (CHCl$_3$) 3606, 3411, 3009, 2972, 2875, 1621, 1490 cm$^{-1}$; $^1$H NMR (300 Mhz, CDCl$_3$) δ7.65 (d, 1H, J=8.0 Hz) 7.42 (s, 1H), 7.06 (dd, 1H, J=1.0, 8.2 Hz), 4.92 (quintet, 1H, J=7.7 Hz), 4.84 (s, 2H), 2.98 (q, 2H, J=7.6 Hz), 2.2 (m, 4H), 2.0 (m, 2H), 1.7 (m, 3H), 1.38 (t, 3H, J=7.6 Hz); MS (thermospray, NH$_4$OAc) m/z 245 (M+H$^+$. base); HRMS calcd for C$_{15}$H$_{20}$N$_2$O+H: 245.1654. Found: 245.1675.

H. 1-Cyclopentyl-3-ethyl-1H-indazole-6-carbaldehyde. 106 mg (0.301 mmol, 0.05 equiv) tetrapropylammonium perruthenate (VII) were added to a room temperature suspension of 1.47 g (6.02 mmol, 1.0 equiv) (1-cyyclopentyl-3-ethyl-1H-indazol-6-yl)-methanol, 1.06 g (9.03 mmol, 1.5 equiv) N-methylmorpholine N-oxide and 3.01 g 4A molecular sieves in 12 mL anhydrous CH$_2$Cl$_2$. After 20 minutes the reaction mixture was filtered through a short column of silica gel (eluted with CH$_2$Cl$_2$). Fractions containing product were concentrated, and the residue chromatographed on a silica gel column (15% ethyl acetate/hexanes, flash) to give 924 mg (63% of a pale yellow solid: mp 41° C.; IR (KBr) 3053, 2966, 2872, 2819, 1695 cm$^{-1}$; $^1$H NMR (300 MHz, CDCl$_3$) δ 10.13 (s, 1H), 7.93 (d, 1H, J-0.9 Hz), 7.77 (d, 1H, J=8.4 Hz), 7.60 (dd, 1H, J=1.2, 8.4 Hz), 5.00 (quintet, 1H, J=7.5 Hz), 3.01 (q, 2H, J-7.6 Hz), 2.2 (m, 4H), 2.0 (m, 2H), 1.7 (m, 2H), 1.39 (t, 3H, J=7.5 Hz); MS (Cl, NH$_3$) m/z 243 (M+H$^+$, base); Anal. calcd for C$_{15}$H$_{18}$N$_2$O: C, 74.35; H, 7.49; N, 11.56. Found: C, 74.17; H, 7.58; N, 11.79.

PREPARATION 2

1-Cyclopentyl-3-ethyl-1H-indazole-6-carbaldehyde

A. 4-Bromo-2-nitro-1-propyl-benzene. 125 g (628 mmol, 1.0 equiv) 1-bromo-4-propyl-benzene was added in one portion to a 10° C. solution of 600 mL conc. H$_2$SO$_4$ and 200 mL H$_2$O. With vigorous mechanical stirring, an ambient temperature mixture of 43.2 mL (691 mmol, 1.1 equiv) conc. HNO$_3$ (69–71%, 16M) in 150 mL conc. H$_2$SO$_4$ and 50 mL H$_2$O was added dropwise over 30 minutes. The ice bath was allowed to warm to ambient temperature, and the reaction stirred at room temperature for 68 hours. The reaction mixture was poured into a 4 L beaker, loosely packed full with crushed ice. After stirring 1 hour, the mixture was transferred to a 4 L separatory funnel and extracted 4×800 mL isopropyl ether. The organic extracts were combined, washed 3×800 mL H$_2$O, 1×500 mL brine, and dried over Na$_2$SO$_4$. Filtration, concentration of filtrate and drying gave 150 mL of a yellow liquid, which was purified by silica gel chromatography (2 columns, 3 kg silica gel each, 2% ethyl acetate/hexanes) to afford 63.9 g (42%) of a yellow liquid. The desired regioisomer is the less polar of the two, which are formed in a 1:1 ratio. bp 108° C., 2.0 mm; IR (CHCl$_3$) 3031, 2966, 2935, 2875, 1531, 1352 cm$^{-1}$; $^1$H NMR (300 MHz, CDCl$_3$) δ 8.01 (d, 1H, J=2.1 Hz), 7.62 (dd, 1H, J=2.1, 8.3 Hz) 7.23 (d, 1H, J=8.3 Hz), 2.81 (m, 2H), 1.67 (m, 2H), 0.98 (t, 3H, J=7.4 Hz); $^{13}$C NMR (75.5 MHz, CDCl$_3$) δ 13.94,23.74, 34.43, 119.6, 127.4, 133.3, 135.7, 136.4, 149.8; GCMS (EI) m/z 245/243 (M+.), 147 (base); HRMS calcd for C$_9$H$_{10}$NO$_2$Br+H: 243.9973. Found: 243.9954.

B. 5-Bromo-2-propyl-phenylamine. 121 g (639 mmol, 3.0 equiv) of stannous chloride (anhydrous) were added in one portion to a room temperature solution of 51.9 g (213 mmol, 1.0 equiv) 4-bromo-2-nitro-1-propyl-benzene in 1200 mL absolute ethanol and 12 mL (6 equiv) H$_2$O. After 24 hours at room temperature, most of the ethanol was removed on a rotary evaporator. The residue was poured into a 4 L beaker, ¾ full with crushed ice and H$_2$O. 150 g of NaOH pellets were added portionwise, with stirring, until the pH=10 and most of the tin hydroxide has dissolved. The mixture was divided in half, and each half extracted 2×750 mL ethyl acetate. All four ethyl acetate extracts were combined, washed 1×500 mL each 1 N NaOH, H$_2$O, and brine, then dried over Na$_2$SO$_4$. Filtration, concentration of filtrate and drying gave a yellow liquid, which was purified on a 1.2 kg silica gel column (1:12 ethyl acetate/hexanes) to give 41.83 g (92%) of a pale yellow liquid: IR (CHCl$_3$) 3490, 3404, 3008, 2962, 2933, 2873, 1620, 1491 cm$^{-1}$; $^1$H NMR (300 MHz, CDCl$_3$) δ 6.8–6.9 (m, 3H), 3.90 (br s, 2H), 2.42 (m, 2H), 1.62 (m, 2H), 0.99 (t, 3H, J=7.3 Hz); GCMS (EI) m/z 215/213 (M+.), 186/184 (base); Anal. calcd for C$_9$H$_{12}$NBr: C, 50.49; H, 5.65; N, 6.54. Found: C, 50.77; H, 5.70; N, 6.50.

C. 6-Bromo-3-ethyl-1H-indazole. 49.22 g (230 mmol, 1.0 equiv) 5-bromo-2-propyl-phenylamine were placed in a 3 L flask and chilled in an ice bath. A 0° C. solution of 57.5 mL (690 mmol, 3.0 equiv) conc. HCl in 165 mL H$_2$0 was added, and the resulting solid mass which formed was ground up until a fine white suspension resulted. 100 mL more H$_2$O were added, then a solution of 15.9 g (230 mmol, 1.0 equiv) sodium nitrite in 75 mL H$_2$O was added dropwise over 10 minutes. The ice bath was removed, and the reaction allowed to stir at room temperature for 30 minutes. The reaction mixture was then filtered through a sintered glass funnel, precooled to 0° C. The filtrate was chilled in an ice bath, and with mechanical stirring, a 0° C. solution/suspension of 32.8 g (313 mmol, 1.36 equiv) ammonium tetrafluorobrate in 110 mL H$_2$O was added dropwise over 10 minutes. The thick white suspension which formed (aryl diazonium tetrafluoroborate salt) was allowed to stir 1.5 hours at 0° C. The mixture was then filtered, and the solid washed 1×200 mL 5% aq. NH$_4$BF$_4$ (cooled at 0° C.), 1×150 mL CH$_3$OH (cooled to 0° C.), then 1×200 mL Et$_2$O. Drying at high vacuum, ambient temperature for 1 hour gave 54.47 g (76%) of the diazonium salt, an off-white solid.

1500 mL of ethanol free chloroform were placed in a 3 flask, then 34.16 g (348 mmol, 2.0 equiv) potassium acetate (powdered and dried) and 2.3 g (8.7 mmol, 0.05 equiv) 18-crown-6 were added. After 10 minutes, the diazonium salt was added in one portion, and the reaction mixture allowed to stir at room temperature under nitrogen atmosphere for 18 hours. The mixture was then filtered, the solid washed 2× with CHCl$_3$, and the filtrate concentrated to give 47 g of crude product (brown crystals). Silica gel chromatography (1.2 kg silica gel, ethyl acetate/hexanes gradient 15%, 20%, 40%) gave 21.6 g (55% for second step, 42% overall) of tan crystals: mp 112–114° C.; IR (KBr) 3205, 3008, 2969, 2925, 1616, 1340, 1037 cm$^{-1}$; $^1$H NMR (300 MHz, CDCl$_3$) δ 9.86 (br s, 1H), 7.61 (d, 1H, J=1.3 Hz), 7.57 (d, 1 H, J=8.4 Hz), 7.24 (dd, 1H, J=1.5, 8.6 Hz), 2.99 (q, 2H, J=7.6 Hz), 1.41 (t, 3H, J=7.6 Hz); MS (Cl, NH$_3$) m/z 227/225 (M+H$^+$, base); Anal. calcd for C$_9$H$_9$N$_2$Br: C, 48.02; H, 4.03; N, 12.45. Found: C, 48.08; H, 3.87; N, 12.45.

D. 6-Bromo-1-cyclopentyl-3-ethyl-1H-indazole. 2.46 g (61.4 mmol, 1.05 equiv) sodium hydride, 60% oil dispersion, were added in 0.5 g portions to a 10° C. solution of 13.17 g (58.5 mmol, 1.0 equiv) 6-bromo-3-ethyl-1H-indazole in 500 mL anhydrous DMF. The mixture was stirred at ambient temperature for 20 minutes, then a solution of 8.8 mL (81.9 mmol, 1.4 equiv) cyclopentyl bromide in 10 mL anhydrous DMF was added dropwise. After 18 hours, the reaction mixture was poured into 2 L H$_2$O and extracted 2×1 L ethyl acetate. The organic extracts were combined, washed 2×750 mL H$_2$O, 1×500 mL brine, and dried over Na$_2$SO$_4$. Filtration, concentration of filtrate and drying gave 20.7 g of crude product, which was purified on a silica gel column (1.1 kg silica gel, 3% ethyl acetate/ hexanes) to give 10.6 g (62%) of an amber liquid: IR (CHCl$_3$) 2972, 2875, 1606, 1501, 1048 cm$^{-1}$; $^1$H NMR (300 mHz, CDCl$_3$) δ 7.56 (d, 1H, J=1.3 Hz), 7.52 (d, 1H, J=8.7 Hz), 7.17 (dd, 1H, J=1.5, 8.5 Hz), 4.83 (quintet, 1H, J=7.6 Hz), 2.96 (q, 2H, J=7.6 Hz), 2.15 (m, 4H), 2.0 (m, 2H), 1.65 (m, 2H), 1.36 (t, 3H, J=7.7 Hz); MS (thermospray, NH$_4$OAc) m/z 295/293 (M+H+, base); Anal. calcd for C$_{14}$H$_{17}$N$_2$Br: C, 57.35; H, 5.84; N, 9.55. Found: C, 57.48; H, 5.83; N, 9.90.

E. 1-Cyclopentyl-3-ethyl-1H-indazole-6-carbaldehyde. 11.6 mL (28.4 mmol, 1.0 equiv) n-BuLi, 2.45 M in hexanes, were added to a −78° C. solution of 8.32 g (28.4 mmol, 1.0 equiv) 6-bromo-1-cyclopentyl-3-ethyl-1H-indazole in 200 mL anhydrous THF. After 30 min. at −78° C., 8.8 mL (114 mmol, 4.0 equiv) anhydrous DMF were added dropwise, and the reaction mixture was allowed to stir an additional 30 minutes at −78° C. The mixture was warmed to room temperature over 1 hour, then 125 mL 1N HCl were added. After stirring for 10 minutes, most of the THF was removed on a rotary evaporator. The residue was diluted with 500 mL H$_2$O, and extracted 2×250 mL ethyl acetate. The organic extracts were combined, washed 1×100 mL H$_2$O, 1×100 mL brine, and dried over Na$_2$SO$_4$. Filtration, concentration of filtrate and drying gave a yellow oil, which was purified on silica gel column (15% ethyl acetate/hexanes, gravity) to give 4.70 g (68%) of a yellow crystalline solid: $^1$H NMR (300 MHz, CDCl$_3$) identical to the spectrum of the title compound from Preparation 1.

EXAMPLE 1

(+)-1-(1-Cyclopentyl-3-ethyl-1H-indazol-6-yl)-1,2-di-pyridin-4-yl-ethanol

A. (1-Cyclopentyl-3-ethyl-1H-indazol-6-yl)-pyridin-4-yl-methanone. 1.53 mL (3.83 mmol, 1.1 equiv) n-BuLi, 2.5 M in hexanes, were added dropwise to a −78° C. solution of 1.02 g (3.48 mmol, 1.0 equiv) 6-bromo-1-cyclopentyl-3-ethyl-1H-indazole in 10 mL anhydrous THF. After 10 minutes, a room temperature suspension of 417 mg (4.00 mmol, 1.15 equiv) 4-cyanopyridine in 10 mL anhydrous THF was added, and the reaction mixture allowed to stir at −78° C. for 45 minutes. The reaction mixture was then allowed to warm to −10° C. over 30 minutes 12 mL of 2N HCl were added, and the reaction stirred at room temperature for 30 minutes. The mixture was poured into 75 mL H$_2$O, basified to pH 14 with 1 N NaOH, and extracted 2×60 mL ethyl acetate. The organic extracts were combined, washed 1×25 mL brine, and dried over Na$_2$SO$_4$. Filtration, concentration of filtrate and drying gave 1.19 g of a amber oil, which was purified on a silica gel column (50% ethyl acetate/hexanes) to give 749 mg (67%) of an off-white solid. A small sample was recrystallized from ethyl acetate/ hexanes for analytical data: mp 129–131° C.; MS (Cl, NH$_3$) m/z 320 (M+H$^+$, base).

B. (+)-1-(1-Cyclopentyl-3-ethyl-1H-indazol-6-yl)-1,2-di-pyridin-4-yl-ethanol. 952 μL (2.38 mmol, 1.0 equiv) n-BuLi, 2.5 M in hexanes, were added dropwise to a −78° C. solution of 231 μL (2.38 mmol, 1.10 equiv) 4-methylpyridine in 10 mL anhydrous THF. After 30 minutes, a room temperature solution of 690 mg 92.16 mmol, 1.0 equiv) (1-cyclopentyl-3-ethyl-1H-indazol-6-yl)-pyridin-4-yl-methanone in 5 mL anhydrous THF was added over 5 minutes. The reaction mixture was allowed to stir 1 hour at −78° C., then ½ hour at room temperature. 50 mL H$_2$O were added, and the mixture extracted 3×50 mL ethyl acetate. The organic extracts were combined, washed 1×50 mL brine, and dried over Na$_2$SO$_4$. Filtration, concentration of filtrate and drying gave a yellow solid, which was purified on a silica gel column (5% CH$_3$OH/CH$_2$Cl$_2$) to give 248 mg (28%) of white crystals: mp 208–211° C.; MS (Cl, NH$_3$) m/z 413 (M+H$^+$, base).

EXAMPLE 2

1-Cyclopentyl-6-(1,2-di-pyridin-4-yl-vinyl)-3-ethyl-1H-indazole 191 mg (0.463 mmol, 01equiv) 1-(1-cyclopentyl-3-ethyl-H-indazol-6-yl)-1,2-di-pyridin-4-yl-ethanol, 220 mg (1.16 mmol, 2.5 equiv) p-toluenesulfonic acid and 30 mL anhydrous toluene were placed in a flask fitted with a Dean-Stark trap and heated to reflux under nitrogen atmosphere. After 24 hours, the reaction mixture was cooled to room temperature, diluted with 50 mL ethyl acetate, washed 2×15 mL 1 N NaOH, 1×15 mL $H_2O$, 1×15 mL brine, and dried over $Na_2SO_4$. Filtration, concentration of filtrate and drying gave 180 mg of an off white solid, which was purified on a silica gel column (4% $CH_3OH/CH_2Cl_2$) to give 53 mg (29%) of a yellow amorphous solid: $^1H$ NMR (300 MHz, $CDCl_3$) δ 8.62 (br s, 2H0, 8.42 (br s, 2H), 7.63 (dd, 1H, J=0.6, 8.4 Hz), 7.2 (m, 3H), 7.0 (m, 2H), 6.9 (m, 2H), 4.81 (quintet, 1H, J=7.6 Hz), 2.98 (q, 2H, J=7.6 Hz), 2.2 (m, 4H), 2.0 (m, 2H), 1.7 (m, 2H), 1.37 (t, 3H, J=7.6 Hz); MS (Cl, $NH_3$) m/z 395 (M+H$^+$, base).

EXAMPLE 3

(+)-1-Cyclopentyl-6-(1,2-di-pyridin-4-yl-ethyl)-3-ethyl-1H-indazole hydrochloride A mixture of 51 mg (0.129 mmol, 1.0 equiv) 1-cyclopentyl-6-(1,2-di-pyridin-4-yl-vinyl)-3-ethyl-1H-indazole and 50 mg 10% Pd/C in 7.5 mL ethanol and 250 μL triethylamine was placed on a Parr® hydrogenation apparatus and shaken under 25 psi $H_2$ at room temperature for 3.5 hour. The reaction mixture was then filtered through Celite®, and the filtrate concentrated on a rotary evaporator and purified on a silica gel column (5% $CH_3OH/CH_2Cl_2$) to give 40 mg (78%) of a white solid. This solid was dissolved in 4 mL ether and 202 μL (2.0 equiv) 1N HCl in ether were added. After 15 minutes, the mixture was filtered, and the filtrant dried at high vacuum, room temperature to give 31 mg (66%) of a yellow powder. mp 245–254° C. (dec); Anal. calcd for $C_{26}H_{28}N_4 \cdot 2HCl \cdot \frac{3}{4}H_2O$: C, 64.86; H, 6.60; N, 11.64. Found: C, 64.75; H, 6.43; N, 11.57.

EXAMPLE 4

(+)-1-(1-Cyclopentyl-3-ethyl-1H-indazol-6-yl)-1-phenyl-2-pyridin-4-yl-ethanol A. (1-Cyclopentyl-3-ethyl-1H-indazol-6-yl)-phenyl-methanol. 3.4 mL (6.08 mmol, 1.0 equiv) phenyl lithium, 1.8 M in cyclohexane/ether, were added dropwise to a –78° C. solution of 1.34 g (5.53 mmol, 1.0 equiv) 1-cyclopentyl-3-ethyl-1H-indazole-6-carbaldehyde in 10 mL anhydrous THF. After 30 minutes at –78° C., the reaction mixture was allowed to warm to room temperature over 3 hour. 75 mL $H_2O$ were added, and the mixture extracted 3×50 mL ethyl acetate. The organic extracts were combined, washed 1×50 mL $H_2O$, 1×50 ML brine, and dried over $Na_2SO_4$. Filtration, concentration of filtrate and drying gave 1.92 g of a yellow oil, which was purified on a silica gel column (20% ethyl acetate/hexanes) to give 1.49 g (84%) of a pale yellow oil, which crystallized on standing: mp 88–91° C.; MS (Cl, $NH_3$) m/z 321 (M+H$^+$, base); Anal. calcd for $C_{21}H_{24}N_2O$: C, 78.72; H, 7.55; N, 8.74. Found: C, 78.21; H, 7.71; N, 8.82.

B. (1-Cyclopentyl-3-ethyl-1H-indazol-6-yl)-phenyl-methanone. 72 mg (0.204 mmol, 0.05 equiv) tetrapropylammonium perruthenate (VII) were added to a room temperature suspension of 1.308 g (4.08 mmol, 1.0 equiv) (1-cyclopentyl-3-ethyl-1H-indazol-6-yl)-phenyl-methanol, 717 mg (6.12 mmol, 1.5 equiv) N-methylmorpholine N-oxide and 2.5 g 4A molecular sieves in 25 mL anhydrous $CH_2Cl_2$. After 1 hour, the reaction mixture was filtered through a short column of silica gel (eluted with 100 mL $CH_2Cl_2$, then 75 mL ethyl acetate). Fractions containing product were concentrated, and dried at high vacuum, room temperature to give 1.28 g (98%) of a white crystalline solid: mp 75–77° C.; MS (Cl, $NH_3$) m/z 319 (M+H$^+$, base).

C. (+)-1-(1-Cyclopentyl-3-ethyl-1H-indazol-6-yl)-1-phenyl-2-pyridin-4-yl-ethanol. This compound was prepared using the method of example 1, using 1.22 g (3.83 mmol, 1.0 equiv) (1-cyclopentyl-3-ethyl-1H-indazol-6-yl)-phenyl-methanone as starting material, to give 1.06 g (67%) of a white crystalline solid: mp 175–177° C.; MS (Cl, $NH_3$) m/z 412 (M+H$^+$, base).

EXAMPLE 5

1-Cyclopentyl-3-ethyl-6-(1-phenyl-2-pyridin-4-yl-vinyl)-1H-indazole 1.00 g (2.43 mmol, 1.0 equiv) (±)-1-(1-cyclopentyl-3-ethyl-1H-indazol-6-yl)-1-phenyl-2-pyridin-4-yl-ethanol, 578 mg (3.04 mmol, 1.25 equiv) p-toluenesulfonic acid and 25 mL anhydrous toluene were placed in a flask fitted with a Dean-Stark trap and heated to reflux under nitrogen atmosphere. After 7 hours, the reaction mixture was cooled to room temperature and allowed to stir for 72 hours. The reaction mixture was diluted with 200 mL $H_2O$ and 100 mL 1N NaOH, and extracted 2×100 mL ethyl acetate. The organic extracts were combined, washed 1×50 mL each $H_2O$, brine, and dried over $Na_2SO_4$. Filtration, concentration of filtrate and drying gave a yellow oil, which was purified on a silica gel column (2.5% $CH_3OH/CH_2Cl_2$) to give 0.92 g (95%) of a white amorphous solid. A small sample was crystallized from ethyl acetate/hexanes to give 27 mg white needles: mp 134–1 36° C.; Anal. calcd for $C_{27}H_{27}N_3$: C, 82.41; H, 6.92; N, 10.68; Found: C, 82.31; H, 7.17; N, 10.80.

EXAMPLE 6

(+)-1-Cyclopentyl-3-ethyl-6-(1-phenyl-2-pyridin-4-yl-ethyl)-1H-indazole hydrochloride This compound was prepared according to the method of Example 3 using 0.87 g (2.21 mmol, 1.0 equiv) 1-cyclopentyl-3-ethyl-6-(1-phenyl-2-pyridin-4-yl-vinyl)-1H-indazole as starting material, to give 550 mg (59%) pale yellow powder: mp 193–196° C.; Anal. calcd for $C_{27}H_{29}N_3 \cdot HCl$: C, 75.06; H, 7.00; N, 9.73. Found: C, 73.97; H, 7.30; n, 9.77.

What is claimed is:

1. A compound of Formula (I)

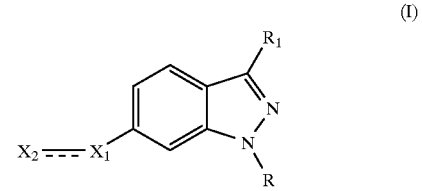

or a pharmaceutically acceptable salt thereof, wherein:
the broken line indicates a single or double bond;
$X_1$ is —$CR_2R_3$ where said broken line indicates a single bond or —$CR_3$ where said broken line indicates a double bond;

$X_2$ is —$CR_5R_7R_8$ or —$C(=NOR_{11})R_{12}$ where said broken line indicates a single bond or —$CR_7R_8$ where said broken line indicates a double bond;

R is H, $C_1$–$C_6$ alkyl, —$(CH_2)_m(C_3$–$C_7$ cycloalkyl), —$(CH_2)_m$-pyridyl, wherein m is 0 to 2, ($C_1$–$C_6$ alkoxy) $C_1$–$C_6$ alkyl, $C_2$–$C_6$ alkenyl, or —$(Z_1)_b(Z_2)C(C_6$–$C_{10}$ aryl) wherein b and c are independently 0 or 1, $Z_1$ is $C_1$–$C_6$ alkylene or $C_2$–$C_6$ alkenylene, and $Z_2$ is O, S, $SO_2$, or $NR_5$, and wherein said R groups are optionally substituted by one or more substituents independently selected from the group consisting of halo, hydroxy, $C_1$–$C_5$ alkyl, $C_2$–$C_5$ alkenyl, $C_1$–$C_5$ alkoxy, $C_3$–$C_6$ cycloalkoxy, trifluoromethyl, nitro, —$CO_2R_5$, —$C(O)NR_5R_6$, —$NR_5R_6$ and —$SO_2NR_5R_6$;

$R_1$ is H, $C_1$–$C_7$ alkyl, $C_2$–$C_3$ alkenyl, phenyl, $C_3$–$C_7$-cycloalkyl, or ($C_3$–$C_7$ cycloalkyl)$C_1$–$C_2$ alkyl, wherein said alkyl, alkenyl and phenyl $R_1$ groups are optionally substituted by 1 to 3 substituents independently selected from the group consisting of methyl, ethyl, trifluoromethyl, and halo;

$R_2$ is H, hydroxy, halo or –$OR_9$;

$R_3$ is independently selected from the group consisting of —$CO_2(CH_2)_n$-phenyl, —$C(Y)NR_5(CH_2)_n$-phenyl, —$(CH_2)_n$-phenyl, and —$(CH_2)_n$-pyridyl, wherein n is 0 to 3, each $R_3$ group is optionally substituted by 1 to 3 $R_4$ groups, and each $R_3$ group is optionally substituted by one $R_{10}$ group;

$R_4$ is independently selected from the group consisting of halo, cyano, nitro, $C_1$–$C_6$ alkyl, $C_2$–$C_6$ alkenyl, —$OR_5$, $C_3$–$C_7$ cycloalkoxy, —$NR_5R_6$, —$NR_5OR_6$, —$S(O)_mR_5$ wherein m is 0 to 2, —$CO_2R_5$, —$C(O)R_5$, —$SO_2NR_5R_6$, —$C(O)NR_5R_6$, —$CR_5R_6SO_2NR_5R_6$, —$CR_5R_6C(O)NR_5R_6$, —$NHSO_2R_5$, —$NHSO_2NR_5R_6$, —$NHC(O)NR_5R_6$, —$NHC(O)(C_1$–$C_6$ alkyl) and —$NHC(O)O(C_1$–$C_6$ alkyl);

$R_5$ and $R_6$ are each independently H or $C_1$–$C_6$ alkyl;

$R_7$ is $R_3$, 2-oxo-pyridyl, 3-oxo-pyridyl, or 4-oxo-pyridyl, wherein each of said $R_7$ groups is optionally substituted by 1 to 3 $R_4$ groups;

$R_8$ is $R_5$, cyano, or —$(CH_2)_p(C_6$–$C_{10}$ aryl), wherein p is 1 to 3 and wherein said $R_8$ substituents are optionally substituted by 1 to 3 $R_4$ substituents;

$R_9$ is formyl, carbamoyl, thiocarbamyl, $C_1$–$C_6$ alkyl, $C_2$–$C_6$ alkenyl, ($C_1$–$C_4$ alkoxy)$C_1$–$C_4$ alkyl, or $C_1$–$C_6$ alkanoyl, wherein the alkyl moieties of said $R_9$ groups are optionally substituted by 1 to 3 substituents independently selected from halo, hydroxy, and $C_1$–$C_4$ alkoxy;

$R_{10}$ is cyclobutyl, cyclopentyl, cyclohexyl, 2-cyclobuten-1-yl, 2-cyclopenten-1-yl, 3-cyclopenten-1-yl, 2,4-cyclopentadien-1-yl, or 3,5-cyclohexadien-1-yl, wherein said $R_{10}$ substituents are optionally substituted by 1 or 2 $C_1$–$C_2$ alkyl;

$R_{11}$ is H, $C_1$–$C_6$ alkyl, $C_2$–$C_6$ alkenyl, $C_2$–$C_6$ alkynyl, —$C(Y)NR_5R_6$, —$C(Y)NH(C_6$–$C_{10}$ aryl), —$C(Y)(C_1$–$C_6$ alkoxy), —$C(Y)(C_6$–$C_{10}$ aryloxy), or —$C(Y)(C_1$–$C_6$ alkyl);

$R_{12}$ is phenyl or pyridinyl, wherein said $R_{12}$ substituents are optionally substituted by 1 to 3 substituents independently selected from halo, $C_1$–$C_4$ alkyl, hydroxy, $C_1$–$C_4$ alkoxy, —$NR_5R_6$ and —$S(O)_mR_5$ wherein m is 0 to 2; and, Y is O or S.

2. A compound of claim 1 wherein $R_1$ is ethyl and R is cyclopentyl, cyclohexyl, or $C_6$–$C_{10}$ aryl.

3. A compound of claim 2 wherein $R_3$ is —$(CH_2)_n$-phenyl, or —$(CH_2)_n$-pyridyl, wherein n is 0 to 3.

4. A compound of claim 3 wherein $R_3$ is phenyl or pyridin-4-yl.

5. A compound of claim 2 wherein $R_7$ is —$(CH_2)_n$-pyridyl, wherein n is 0 to 3.

6. A compound of claim 5 wherein $R_7$ is pyridin-4-yl.

7. A compound of claim 1 wherein the broken line indicates a single bond, $R_2$ is H, $R_3$ is phenyl, 3-methyl-phenyl, 4-pyridyl, or 2-methoxy-phenyl, $R_5$ is H, $R_8$ is H, and $R_7$ is 4-pyridyl or 3,5-dichloro-4-pyridyl.

8. A compound of claim 1 wherein the broken line indicates a double bond, $R_3$ is phenyl, 4-methoxy-phenyl, 4-fluoro-phenyl, 4-trifluoromethyl-phenyl or 2-methoxy-phenyl, $R_8$ is H, and $R_7$ is 4-pyridyl.

9. A compound of claim 1 wherein the broken line indicates a single bond, $R_2$ is H, $R_5$ is H, $R_8$ is cyano, and $R_7$ is 4-pyridyl optionally substituted by 1 or 2 chloro groups or —$NR_5R_6$.

10. A compound of claim 1 wherein the broken line indicates a double bond, $R_8$ is H, and $R_7$ is 4-pyridyl or phenyl optionally substituted by 1 or 2 chloro groups.

11. A compound of claim 1 wherein the broken line indicates a single bond, $R_2$ is H, and $X_2$ is —$C(=NOR_{11})R_{12}$.

12. A compound of claim 1 wherein said compound is selected from the group consisting of:

1-(1-cyclopentyl-3-ethyl-1H-indazol-6-yl)-1,2-di-pyridin-4-yl-ethanol;

1-cyclopentyl-6-(1,2-di-pyridin-4-yl-vinyl)-3-ethyl-1H-indazole;

1-cyclopentyl-6-(1,2-di-pyridin-4-yl-ethyl)-3-ethyl-1H-indazole;

1-(1-cyclopentyl-3-ethyl-1H-indazol-6-yl)-1-phenyl-2-pyridin-4-yl-ethanol;

1-cyclopentyl-3-ethyl-6-(1-phenyl-2-pyridin-4-yl-vinyl)-1H-indazole;

1-cyclopentyl-3-ethyl-6-(1-phenyl-2-pyridin-4-yl-ethyl)-1H-indazole;

and pharmaceutically acceptable salts of the foregoing compounds.

13. A compound of claim 1 wherein said compound is selected from the group consisting of:

1-(1-cyclohexyl-3-ethyl-1H-indazol-6-yl)-1,2-di-pyridin-4-yl-ethanol;

1-cyclohexyl-6-(1,2-di-pyridin-4-yl-vinyl)-3-ethyl-1H-indazole;

1-cyclohexyl-6-(1,2-di-pyridin-4-yl-ethyl)-3-ethyl-1H-indazole;

1-(1-cyclohexyl-3-ethyl-1H-indazol-6-yl)-1-phenyl-2-pyridin-4-yl-ethanol;

1-cyclohexyl-3-ethyl-6-(1-phenyl-2-pyridin-4-yl-vinyl)-1H-indazole;

1-cyclohexyl-3-ethyl-6-(1-phenyl-2-pyridin-4-yl-ethyl)-1H-indazole;

and pharmaceutically acceptable salts of the foregoing compounds.

14. A pharmaceutical composition for the inhibition of phosphodiesterase (PDE) type IV or the production of tumor necrosis factor (TNF) comprising a therapeutically effective amount of a compound of Formula (I) as defined in claim 1 and a pharmaceutically acceptable carrier.

15. A pharmaceutical composition for the prevention or treatment of asthma, acute respiratory distress syndrome, chronic pulmonary inflammatory disease, bronchitis, or chronic obstructive airway disease in a mammal in need of such treatment comprising a therapeutically effective amount of a compound of Formula (I) as defined in claim 1 together with a pharmaceutically acceptable carrier therefor.

16. A method of treating or preventing asthma or a disease related thereto by inhibiting phosphodiesterase type IV (PDE4) or inhibiting the production of tumor necrosis factor (TNF) in a mammal in need of such treatment which comprises administering to said mammal a therapeutically effective amount of a compound of Formula (I) as defined in claim 1.

17. A method of claim 16 wherein the disease is selected from acute respiratory distress syndrome, chronic pulmonary inflammatory disease, bronchitis, and chronic obstructive airway disease.

* * * * *